United States Patent [19]

Schlosser et al.

[11] Patent Number: 4,632,827
[45] Date of Patent: Dec. 30, 1986

[54] PEST CONTROL COMPOSITIONS

[75] Inventors: Manfred Schlosser, Lausanne; Jakob Brassel, Lupsingen, both of Switzerland

[73] Assignee: Ciba-Geigy Corporation, Ardsley, N.Y.

[21] Appl. No.: 736,002

[22] Filed: May 20, 1985

[30] Foreign Application Priority Data

May 25, 1984 [CH] Switzerland ............ 2572/84
Apr. 29, 1985 [CH] Switzerland ............ 1813/85

[51] Int. Cl.$^4$ .................. A61K 31/74; A01N 25/00
[52] U.S. Cl. ............................ 424/78; 424/84; 514/63
[58] Field of Search ............ 556/482; 424/78, 84; 514/63

[56] References Cited

U.S. PATENT DOCUMENTS 4,198,533 4/1980 Carney et al. ............ 556/482 X
4,228,093 10/1980 Carney et al. ............ 556/482
4,357,474 11/1982 Carney et al. ............ 556/482

*Primary Examiner*—Paul F. Shaver
*Attorney, Agent, or Firm*—Edward McC. Roberts; Kevin T. Mansfield

[57] ABSTRACT

Use of trans,trans-8,10-dodecadien-1-yloxysilanes of the formula I

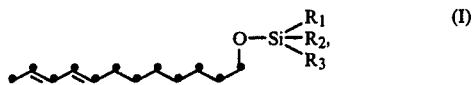

wherein $R_1$ and $R_2$ independently of one another are each a $C_1$–$C_6$-alkyl group, and $R_3$ is a $C_1$–$C_6$-alkyl group or the phenyl group, as a sexual pheromone for the controlling, or the monitoring and early recognition, of Cydia pomonella; compositions containing these compounds, and methods of application; as well as novel compounds of the formula I in which $R_1$ and $R_2$ are a $C_1$–$C_6$-alkyl group, and $R_3$ is a $C_2$–$C_6$-alkyl group or the phenyl group, and also the production thereof.

17 Claims, No Drawings

PEST CONTROL COMPOSITIONS

The present invention relates to the use of trans, trans-8,10-dodecadien-1-yloxysilanes for controlling Cydia pomonella (Laspeyresia pomonella), as well as to novel compounds belonging to this group.

Cydia pomonella is regarded as being one of the main pests in apple crops. The use of insect attractants (sexual pheromones) is advantageous for controlling Cydia pomonella, and also for the monitoring and thus early recognition of any infestation by this pest. Signal substances of this type take effect at extraordinarily low concentrations, and alter the behaviour of the insects in a manner rendering possible the combatting thereof. By virtue of the application of insect attractants, the treatment of the cultivated areas to be protected with insecticides, which are frequently toxic for warm-blooded animals and for useful insects, can be avoided or at least considerably reduced. These working methods, advantageous also from the ecological standpoint, have already attracted great attention in connection with concepts based on the integral protection of plants.

The use of the natural sexual pheromone of Cydia pomonella, that is to say, trans, trans-8,10-dodecadien-1,ol, for controlling this apple pest is known from Science, 174, 297 (1971). Furthermore, it is known from Tetrahedron Letters 30, 2999–3002 (1972) that the stated dodecadienol can be obtained by hydrolysis of trans, trans-8,10-dodecadien-1-yloxy-trimethylsilane, which is not described therein however as being an insect attractant or as being suitable for controlling pests. It has now been found according to the present invention that, surprisingly, 8,10-dodecadienyloxysilanes themselves are excellent for use as attractants for controlling Cydia pomonella. These compounds are advantageously nontoxic and have a long lasting attractive action.

Accordingly, the present invention suggests the use of trans, trans-8,10-dodecadien-1-yloxysilanes of the formula I

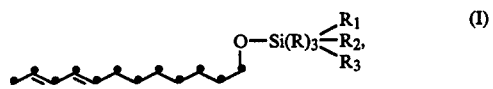

wherein $R_1$ and $R_2$ independently of one another are each a $C_1$–$C_6$-alkyl group, and $R_3$ is a $C_1$–$C_6$-alkyl group or the phenyl group, as sexual pheromones for controlling Cydia pomonella.

There are preferably used compounds of the formula I according to the invention wherein $R_1$ and $R_2$ independently of one another are each a $C_1$–$C_4$-alkyl group, and $R_3$ is a $C_1$–$C_4$-alkyl group or the phenyl group. Particularly advantageous is the use of those compounds of the formula I wherein $R_1$, $R_2$ and $R_3$ are each a $C_1$–$C_4$-alkyl group; and those wherein $R_1$ and $R_2$ independently of one another are each methyl, ethyl, n-propyl or n-butyl, and $R_3$ is methyl, ethyl, n-propyl, n-butyl or phenyl. By virtue of their high activity, compounds to be particularly emphasised for use are also those of the formula I wherein $R_1$, $R_2$ and $R_3$ are each methyl or ethyl.

The invention further suggests novel trans, trans-8,10-dodecadien-1-yloxysilanes of the formula I wherein $R_1$ and $R_2$ independently of one another are each a $C_1$–$C_6$-alkyl group, and $R_3$ is a $C_2$–$C_6$-alkyl group or the phenyl group.

To be especially emphasised are those novel compounds of the formula I wherein $R_1$ is a $C_2$–$C_4$-alkyl group, and $R_2$ independently of one another are each a $C_1$–$C_4$-alkyl group, and $R_3$ is a $C_2$–$C_4$-alkyl group or the phenyl group; and those wherein $R_1$, $R_2$ and $R_3$ are each a $C_2$–$C_4$-alkyl group.

Novel compounds of the formula I to be specially emphasised on account of their action are those wherein $R_1$ and $R_2$ are methyl, ethyl, n-propyl or n-butyl, and $R_3$ is ethyl, n-propyl, -n-butyl or phenyl.

The invention suggests in addition compositions for controlling Cydia pomonella, which contain a compound of the formula I together with suitable carriers, solvents, diluents and/or formulation auxiliaries. The compositions containing the sexual pheromones can also be in the form of highly elastic or rubber-like solid mixtures, optionally in the form of dispensers, for example cylindrically or conically shaped moulded parts made of caoutchouc or rubber. The compositions according to the invention can also be formulated as sprayable or brushable, liquid or flowable, preparations, and also as preparations adhering to substrates onto which they are applied, which can or cannot harden, for example with curing or film formation, the film formed being also able to possess elastic characteristics.

The compositions or preparations according to the invention advantageously contain substances and formulation auxiliaries which protect the active ingredient of the formula I against the effect of weather factors, UV radiation and air oxidation, for example antiageing agents, UV absorbers, antioxidants, and so forth. The compositions can also contain adhesives, binders or thickeners, for example based on suitable polymers of copolymers, in order to adapt the compositions to suit given conditions and requirements.

It has been found that the duration of the attractive action on Cydia pomonella depends on the nature of the substituents $R_1$, $R_2$ and $R_3$ in the compounds of the formula I. When, for example, a particularly long duration of activity is desired, there are advantageously selected those compounds of the formula I which contain long-chain alkyl substituents. On the other hand, compounds having short-chain alkyl substituents have a shorter duration of activity. By using mixtures of differently substituted compounds of the formula I, it is possible for example to adjust moreover the duration of activity to suit the particular requirements in practice. The duration of activity can be expressed numerically by the so-called "half-life period". This is the time after which only half of the originally employed amount by weight of the active ingredient is present.

Various systems and practical possibilities of application for insect attractants have already been suggested. These methods are suitable also for the sexual pheromones of the formula I suggested according to the invention for the biological control of Cydia pomonella, and can likewise be used for the monitoring of apple crops and thus for early recognition of any infestation by these pests. The compounds of the formula I and preparations containing them can be used to control the insect pests by the so-called confusion method ("disrupting effect"). In this method, the attractant of the formula I, which has been applied in a crop of apples, acts in such a way that the male moth can no longer locate the female pheromone signal or the female itself. As a result of these effects associated with the disorientation of the insects, the copulation of the insects is prevented or disturbed to such a great extent that virtually no descendants are produced and only small pest populations are able to develop. A drastic reduction in pest infestation thus occurs. The attractant of the formula I can be used also to lure the moths and to then exterminate them by means of traps or snares, and/or insecticides, chemosterilants, and the like. In this regard, the compositions containing the attractant of the formula I according to the invention can also be used together with known insecticides, or insecticides can be incorporated into the compositions. In general, the attractant of the formula I is used in an amount of about 5 to 100 g, preferably 10 to 50 g, for example 20 to 40 g, per hectare of cultivated area.

The attractants of the formula I are generally used as components of preparations or arrangements which ensure a retarded or slow release of these active ingredients. The period during which the active ingredients can be slowly released can extend for example to about 12 weeks. For this purpose, methods are known whereby (a) the attractants are introduced into suitable polymers or copolymers, microencapsulation being especially mentioned, (b) the attractants are incorporated into multi-layered polymeric foil materials, or (c) they are dissolved or dispersed in viscous polymer-formulations. Methods which also have a certain importance are those whereby there are used dispensers filled with the attractant, the dispensers being preferably in the form of hollow fibres or capillaries of plastics material, in order to release into the surrounding atmosphere, over prolonged periods of time, the active ingredients at a practically constant concentration.

The compounds of the formula I suggested within the scope of the present invention can be produced, in a manner known per se [cf. J. Am. Chem. Soc. 74, 1003 (1952)], by reaction of the initially mentioned trans,trans-8,10-dodecadien-1-ol with corresponding trisubstituted chlorosilanes of the formula II:

$$\text{\textasciitilde\textasciitilde\textasciitilde OH} + \text{Cl}-\underset{R_3}{\overset{R_1}{\text{Si}}}-R_2 \longrightarrow \text{(I)}$$

(II)

wherein $R_1$, $R_2$ and $R_3$ have the meanings defined in the foregoing. The starting compounds of the formula II are known or can be produced by processes analogous to known processes.

The reaction is preferably performed under normal pressure and in the presence of a basic acid accepter, for example an amine, such as triethylamine. The reaction can be carried out in the presence of an inert solvent, for example an ether, such as diethyl ether. The reaction temperature is in general within the range of about 0° to 100° C., preferably between 10° and 60° C.

The alkyl groups $R_1$, $R_2$ and $R_3$ in the compounds of the formula I according to the invention can be straight-chain or branched-chain.

Examples of such alkyl groups in the definition of $C_1-C_6$-alkyl according to the invention are for example: methyl, ethyl, n-propyl, i-propyl, the four isomeric butyl groups, and so forth. The groups $R_1$, $R_2$ and $R_3$ can also be different substituents, so that the Si atom in a compound of the formula I can for example be substituted by 2 methyl groups and a t-butyl group, or by two methyl groups and a phenyl group.

EXAMPLE 1

Production of trans,trans-8,10-dodecadien-1-yl-oxytrimethylsilane (compound No. 1)

Method A

A mixture of trans,trans-8,10-dodecadien-1-ol (18.2 g) and sodium amide (4.5 g) in tetrahydrofuran (100 ml) is refluxed for 3 hours and during this time vigorously stirred. After the addition of chlorotrimethylsilane (13.0 g), vigorous stirring at 50° C. is maintained for a further 3 hours. A test is then made by gas chromatography to ensure that the solution contains a further dodecadienol. Diatomaceous earth is subsequently added, and the mixture is filtered, concentrated by evaporation and distilled. The title compound passes over in the boiling range of 77° to 81° C./$3.10^{-6}$ mmHg.

Method B

A mixture of trans,trans-8,10-dodecadien-1-ol (18.2 g), triethylamine (50 ml) and chlorotrimethylsilane (17.5 ml) in diethyl ether (100 ml) is held at 25° C. for 15 hours. The mixture is then filtered, washed with diethyl ether (100 ml), concentrated by evaporation, dissolved in hexane (150 ml) and extracted by shaking with ice-water ($3 \times 100$ ml). After drying (CaSO$_4$), the solvent is evaporated off, and the residue is distilled (boiling range 77° to 80° C./$3.10^{-6}$ mmHg) to thus obtain the title compound ($n_D^{20} = 1.4600$).

EXAMPLE 2

Production of trans,trans-8,10-dodecadien-1-yl-oxytriethylsilane (compound No. 2)

A mixture of trans,trans-8,10-dodecadien-1-ol (1.82 g), triethylamine (3.5 ml) and triethyl-chlorosilane (1.85 ml) is held at 25° C. for 15 hours. After dilution of the mixture with hexane (100 ml), it is thoroughly washed with ice-water ($3 \times 50$ ml), dried (CaSO$_4$), concentrated by evaporation and distilled. The title compound is obtained in the boiling range of 107° to 112° C. ($n_D^{20} = 1.4697$).

By procedures corresponding to those described in the foregoing, there are also obtained the following compounds of the formula I:

| Compound No. | | Physical data |
|---|---|---|
| 3 | 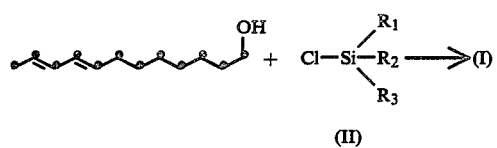 O—Si(n-C$_3$H$_7$)$_3$ | b.p.: 118–125° C./$10^{-5}$ mmHg $n_D^{20} = 1.4690$ |

-continued

| Compound No. | Physical data |
|---|---|
| 4  [structure: chain—O—Si(n-C$_4$H$_9$)$_3$] | b.p.: 135–143° C./10$^{-5}$ mmHg<br>n$_D^{20}$ = 1.4692 |
| 5  [structure: chain—O—Si(CH$_3$)$_2$—(furyl)] | m.p.: 119–125° C./10$^{-5}$ mmHg<br>n$_D^{20}$ 1.5050 |

The following compounds of the formula I can be produced in the manner described above:

Compound No.

6  [structure: chain—O—Si(CH$_3$)(C$_2$H$_5$)(C$_4$H$_9$(t))]

7  [structure: chain—O—Si(CH(CH$_3$)$_2$)(CH$_3$)(C$_2$H$_5$)]

8  [structure: chain—O—Si(C$_4$H$_9$(n))$_2$—(furyl)]

9  [structure: chain—O—Si(CH$_3$)(C$_2$H$_5$)—(furyl)]

EXAMPLE 3

Biological field test

The test area used was an enclosure of 2 hectares on which were standing standard apple trees. There was attached to each of 80 trees distributed over this area a glue-trap for adult males of Cydia pomonella, the traps being loaded with the trans,trans-8,10-dodecadien-1-yloxy-trimethylsilane attractant. The traps used consisted of a delta-shaped hollow body made of paper, which was provided with a slit for letting in the moths, and on the inside with a coating of insect-glue (lime), on which the trapped moths remained firmly fixed. In the paper trap was fitted an attractant-dispenser in the form of a rubber stopper of about 1.5 cm diameter having at the centre a recess into which had been inserted the specifically employed amount of the attractant, dissolved in methylene chloride. The attractant is completely absorbed by the rubber material, and is gradually, that is, in a retarded manner, released. The loss of attractant in a rubber dispenser of this type, commencing with an initial charge of 1.0 mg, amounts after 3 months to about 0.8 mg (half-life period approximately 2 months).

The dispensers were in each case charged with increasing dosages of the attractant of 0.01 to 10.0 mg. The traps, during about two and a half months (2nd June to 19th August), were inspected at regular intervals of time in order to determine the number of trapped moths adhering to the inside walls of the traps. The results obtained are summarised in the following Table I.

TABLE I

| mg of attractant per dispenser | Number of trapped moths (Cydia pomonella) | | | | | |
|---|---|---|---|---|---|---|
| | Inspection of traps after | | | | | Total number of moths trapped |
| | 16 days | 32 days | 43 days | 63 days | 78 days | |
| 0.01 | 0 | 1 | 0 | 0 | 0 | 1 |
| 0.1 | 4 | 3 | 4 | 7 | 6 | 24 |
| 1.0 | 13 | 14 | 18 | 14 | 10 | 69 |
| 10.0 | 28 | 23 | 34 | 39 | 24 | 148 |

EXAMPLE 4

Biological laboratory tests in a wind tunnel

Pheromone and attractant tests with insects in a wind tunnel serve to fundamentally determine numerically, in a reproducible manner, the response of the test insects to, and their behaviour in the presence of, the substances being tested.

The employed wind tunnel, such as was essentially described in the literature (cf. J. R. Hiller and W. L. Roelofs, J. Chem. Ecology, 4, 187–198, 1978), consists basically of a closed tunnel made of transparent material having a rectangular cross-section. On one end-face of the tunnel is located a nozzle with an attractant-dispenser, as is described in Example 3 in the foregoing. At the opposite end-face of the tunnel, there are arranged a short open glass tube to admit the insects, and a take-off platform. A prevailing attractive action of the attractant contained in the dispenser, impinging with the stream of air passed through the nozzle, on the insect in the glass tube, produces in the adult male of Cydia pomonella a state of agitation, which is firstly manifested in motoricity and in a whirring of wings. From the take-off platform, the moth then flies directly and purposive to the attractant source (i.e. the dispenser containing the active substance). In the case of substances without an attractant action, the moth remains motionless in the open glass tube. One moth is placed into the glass tube in each test and, for each compound to be tested, there are carried out on average 30 flight tests in 10 repeats each with 3 moths. The results obtained with attractants compared with those obtained using control batches without attractants are shown in the following Table II.

TABLE II

| Test-compound No. | Amount of test compound on dispenser | % of test insects with flight aimed at dispenser | % of test insects with motoricity and wing whirring |
|---|---|---|---|
| 1 | 100 μg | 43 | 99 |

TABLE II-continued

| Test-compound No. | Amount of test compound on dispenser | % of test insects with flight aimed at dispenser | % of test insects with motoricity and wing whirring |
| --- | --- | --- | --- |
| 1 | 300 μg | 29 | 96 |
| 2 | 300 μg | 44 | 78 |
| 3 | 300 μg | 0 | 67 |
| 4 | 300 μg | 0 | 50 |
| 4 | 3000 μg | 29 | 57 |
| 5 | 300 μg | 40 | 70 |

What is claimed is:

1. A composition for controlling Cydia pomonella, which composition contains a compound of the formula $$\diagup\diagdown\diagup\diagdown\diagup\diagdown\diagup\diagdown\mathrm{O{-}Si}{\begin{matrix}R_1\\R_2,\\R_3\end{matrix}}$$

wherein $R_1$ and $R_2$ independently of one another are each $C_1$–$C_6$-alkyl and $R_3$ is $C_1$–$C_6$-alkyl or phenyl, together with suitable carriers, solvents, diluents and/or formulation auxiliaries.

2. A composition according to claim 1 in the form of a highly elastic or rubber-like solid mixture.

3. A composition according to claim 1 in the form of a sprayable or brushable, liquid or flowable preparation adhering to substrates.

4. A composition according to claim 3 having film-forming and/or curing properties.

5. A composition according to claim 4 having film-forming elastic properties.

6. A method of controlling, or monitoring and early recognition, of Cydia pomonella, which method comprises treating the cultivated area to be protected against infestation by Cydia pomonella with a trans,-trans-8,10-dodecadien-1-yloxysilane of the formula $$\diagup\diagdown\diagup\diagdown\diagup\diagdown\diagup\diagdown\mathrm{O{-}Si}{\begin{matrix}R_1\\R_2,\\R_3\end{matrix}}$$

wherein $R_1$ and $R_2$ independently of one another are each $C_1$–$C_6$-alkyl and $R_3$ is $C_1$–$C_6$-alkyl or phenyl or with a composition containing this compound, whereby said compound is released, in an amount sufficient to be effective as a sexual pheromone, into the surrounding atmosphere.

7. A method according to claim 6, wherein the employed amount of the is 5 to 100 g per hectare.

8. A method of claim 6, wherein the employed amount of the compound is 10 to 50 g per hectare.

9. A method of claim 6, wherein $R_1$ and $R_2$ independently of one another are each $C_1$–$C_4$-alkyl and $R_3$ is $C_1$–$C_4$-alkyl or phenyl.

10. A method of claim 9, wherein $R_1$, $R_2$ and $R_3$ are each $C_1$–$C_4$-alkyl.

11. A method of claim 9, wherein $R_1$ and $R_2$ independently of one another are each methyl, ethyl, n-propyl or n-butyl, and $R_3$ is methyl, ethyl, n-propyl, n-butyl or phenyl.

12. A method of claim 11, wherein $R_1$, $R_2$ and $R_3$ are each methyl or ethyl.

13. The method of claim 12, wherein the compound is trans,trans-8,10-dodecadien-1-yloxy-trimethylsilane.

14. The method of claim 12, wherein the compound is trans,trans-8,10-dodecadien-1-yloxytriethylsilane.

15. The method of claim 11, wherein the compound is trans,trans-8,10-dodecadien-1-yloxytri-n-propylsilane.

16. The method of claim 11, wherein the compound is trans,trans-8,10-dodecadien-1-yloxytri-n-butylsilane.

17. The method of claim 11, wherein the compound is trans,trans-8,10-dodecadien-1-yloxydimethylphenylsilane.

* * * * *